(12) United States Patent
Naidoo

(10) Patent No.: US 6,319,207 B1
(45) Date of Patent: Nov. 20, 2001

(54) INTERNET PLATFORM WITH SCREENING TEST FOR HEARING LOSS AND FOR PROVIDING RELATED HEALTH SERVICES

(76) Inventor: Sharmala Naidoo, Jupiter Strasse 21-416, Bern, 3015 (CH)

( * ) Notice: Subject to any disclaimer, the term of this patent is extended or adjusted under 35 U.S.C. 154(b) by 0 days.

(21) Appl. No.: 09/523,873

(22) Filed: Mar. 13, 2000

(51) Int. Cl.[7] .................................................. A61B 5/00
(52) U.S. Cl. .......................................... 600/559; 600/300
(58) Field of Search ..................................... 600/559, 300

(56) References Cited

U.S. PATENT DOCUMENTS

| | | |
|---|---|---|
| 3,808,354 | 4/1974 | Feezor et al. . |
| 3,974,335 | 8/1976 | Blackledge . |
| 5,143,081 * | 9/1992 | Young et al. ......................... 600/554 |
| 5,811,681 * | 9/1998 | Braun et al. ............................ 73/585 |
| 5,928,160 | 7/1999 | Clark et al. . |
| 6,086,541 | 7/2000 | Rho . |
| 6,167,138 * | 12/2000 | Shennib ................................. 381/60 |

OTHER PUBLICATIONS

"On the Detection of Extremely Small Changes in Sound Intensity", Reprinted from the A.M.A. Archives of Otolaryngology, Feb. 1959, vol. 69, pp. 220–211. Copyright 1959, by American Medical Association, James Jerger, Ph.D.; Joyce Lassman Shedd, M.A. and Earl Harford, M.S.

* cited by examiner

*Primary Examiner*—Eric F. Winakur
*Assistant Examiner*—Pamela Wingood

(74) *Attorney, Agent, or Firm*—Knobbe Martens Olson & Bear LLP

(57) ABSTRACT

An adaptive screening tool for hearing loss for use over the internet. The test is part of a web-based system which providing hearing related information and health services. The system allows users of the internet located anywhere in the world to perform a screening test in the privacy of their own homes or offices. The test is performed well above the threshold level of the user, and screens users for their ability to detect small changes in intensity within bursts of sound delivered to the user through headphones. Users are given a first or preliminary test to establish a base intensity. Then, after the base intensity is established, a second test for hearing loss is presented. The second test asks the user to identify which of a plurality of similar sounds, or stimuli, is different from the others because it has a short duration deviation embedded in it. The deviation or differentiating characteristic may be: a) an increase or decrease in at least a portion of one in a plurality of similar sounds, and/or b) an increase or decrease in the frequency or pitch of at least a portion of one in a plurality of similar sounds and/or c) an increase or decrease in the duration of one of a plurality of similar sounds. The series of sounds, one of which contains a differentiating characteristic, may be designed so that the differentiating characteristic is detectable only by persons with certain kinds of hearing losses. Alternatively or in combination, such additional groups or series of sounds in which one sound of a plurality of similar sounds in the series is capable of being identified only by persons with normal hearing. Based upon the user's score on the screening tests, the user may be directed to a source for further information on how to deal with partial hearing loss.

19 Claims, 6 Drawing Sheets

INTERNET PLATFORM WITH SCREENING TEST FOR HEARING LOSS AND FOR PROVIDING RELATED HEALTH SERVICES

The present invention relates to the providing of health services over the internet. In particular, the present invention relates to an internet platform or portal for providing early diagnosis, through screening, of hearing impairment, and for providing information regarding effective treatment, rehabilitation and monitoring of patients.

BACKGROUND AND SUMMARY OF THE INVENTION

Hearing loss affects people of all ages, and it is conservatively estimated that at least 10% of any population have a hearing disorder. For a young child, early identification of hearing loss facilitates successful integration of that child into society as he or she grows up. The prevelance of hearing loss in the teenage population is steadily rising, due mainly to exposure to dangerous levels of environmental sounds, such as very loud music. Preventative awareness programs play a major role in controlling the number of teenagers affected. In the adult population, good hearing is important to maintaining an active and healthy lifestyle and for purposes of earning a living. As the life expectancy of people increases, and the number of elderly people increases, the negative impact of hearing loss on the quality of life during retirement years has become even more important.

Only about one percent of those with hearing loss seek diagnosis and intervention at an appropriate time. The main reason for this shortcoming is the lack of good information regarding options which are available, where to go for hearing tests, and where to purchase devices which will enable one to hear better. Even though many people have hearing aids, nearly all of those require ongoing monitoring of the effectiveness of those devices, regular testing of the extent of hearing loss, and advice on how to make the best use of the hearing aid in order to maximize the benefit therof.

Typical audiometric tests of hearing are conducted in a relatively quiet room or in a sound proof booth. The health care professional uses an audiometer in the same room, or in an adjacent room with a two way mirror. The aim of the test is to determine the softest level (threshold) at which a sound/tone is heard. The testee is instructed to listen carefully and push a response button or raise their hand or finger each time they hear a sound/tone. A set of headphones is placed over the ears of the 'testee'. The tester begins the test at a comfortable level at a mid frequency and continues the test at octaves from 250 Hz through 8000 Hz. The test is completed at each ear. The results are recorded on an audiogram. The above test may occassionally utilize speech materials; however, frequency specific information is not gleaned.

Early diagnosis of hearing loss is crucial for timely rehabilitation that could improve hearing and allow for improved quality of life for persons at all ages. Some forms of rehabilitation include amplification and assistive listening devices, medical intervention, support services and counselling. A large number of individuals, including children and the elderly, may suspect that they have a hearing loss albeit do not visit a health care center for a full scale evaluation and treatment. The reasons include expense, time, location, reticience, lack of awareness of options, lack of information about consequences of poor hearing, or procrastination. All clinically standard hearing tests to date depend on the expertise of a health care or of a hearing health care professional.

One particular problem of the standard audiometric test method is the reliance on specialized equipment at the site of testing. Over the last decade, a number of technological telecommunication advancements have allowed access to large groups of citizens; these include mobile phones and the internet. Through fixed and mobile internet connections, the internet provides a quick and easy means of reaching masses of the world population in private and retirement homes, schools, hospitals, clinics. In the last year, many health care services have been made available through the internet and end users are becoming more active participants in their health care.

One means of providing a great number of people with hearing health care services is to utilize the internet (fixed, mobile, via satellite or terresterial links). The present invention overcomes the restraints of time, distance, expense of initial hearing screening, and lack of access to vital information from the health care provider. To date, the developement of a hearing test over the internet has been hampered by the problems of sound calibration, i.e., when using the internet, there is no way of knowing the intensity level of the sound reaching the testee's eardrum. The present invention overcomes the obstacles listed above. Further, the invention provides a holistic approach to hearing health care, promotes awareness of hearing loss, and improves the quality of life for all citizens through a multi-lingual internet platform. The service is also accessible through licensed computer software.

The designation "HL" is an acronym for Hearing Level, and is used to refer to sound level measured above the softest level at which sound is heard (0 HL). The designation "SPL" is an acronym for Sound Pressure Level, and is a reference to the absolute value used by acousticians and scientists, and is typically measured with such as a sound level meter. The designation "SL" stands for Sensation Level, and is a reference to the level of decibels (dB) above Hearing Level. For example, if one's threshold for a 1000 Hz sound is 10 dB HL, then 20 SL would be 20 dB above your threshold, making the presentation level 30 dB HL. The presentation levels of the sounds as they are initially recorded is preferably set to 19 dB SL.

The major problem with any type of on-line testing, including testing of hearing through the Internet, is the difficulty with calibrating the sound output at the end users ear. Most testing in standard audiological test batteries depend on absolute calibration. Presentation levels and results are expressed in dB HL or dB SPL and the testing of threshold, i.e., the softest level at which a person hears a pure tone or speech sound. 0–20 dB HL is designated normal hearing across frequencies of 250, 500, 100, 2000, 4000, and 8000 Hz.

Presenting and recording hearing tests and screening over the internet presents difficulties for absolute calibration of signals. Furthermore, the signal can be affected by many variables including computer and internet transmission lines, and transducers used (e.g., headphones or loudspeakers). Threshold testing therefore presents enormous difficulties when used in the orthodox fashion.

The consumer logs onto a website capable of testing in accordance with the present invention, and the consumer is presented with a user-friendly screen in their choice of language, e.g., French, English, Italian, Spanish, Portuguese. The Screening of Hearing link is selected. Simple overview, instructions and requirements for the test (see appendix) are provided, including a hearing screening questionnaire about their health (general and hearing). They use a set of computer headphones (preferably circumaural). A trial run of the testing is available to demonstrate the test sequence and required response from the testee.

The actual testing commences one ear at a time. At the end of the test, the results are clearly outlined, i.e., the testee has either passed the hearing screening, or has failed the hearing screening. The testee can access the nearest hearing health center/clinic for a followup test through on line scheduling of an appointment. They have immediate access to the results of their tests and can be linked to their nearest, local or international health care centers/providers. Their results are logged into an International database. They are also provided with on-line access to information on hearing, hearing loss, rehabilitation, amplification, access to hearing related products and services, and to support systems globally. The test of hearing is provided through an adaptive test on-line or off-line through licensed software.

In the present invention, the problems encountered by previous attempts to test and screen hearing in terms of absolute and threshold levels is avoided. The invention relies on suprathreshold measures to screen hearing, rather than on absolute threshold measures. In this manner the test is self-calibrating. The test methodology of the present invention uses presentation levels above threshold, and relies on established and validated physiological attributes of the hearing mechanism and normative data for normal and abnormal hearing. The invention focuses on the individual's ability to differentiate small differences in intensity, duration and frequency levels.

One of the tests performed with the system of the present invention recognizes that persons with normal hearing may not be able to detect small differences between otherwise similar sounds, e.g., a short duration 1 dB increase in intensity; whereas, those with sensorineural hearing losses will be able to detect the differences. The present invention presents a plurality of sounds, at comfortable levels, which can be heard by persons with sensorineural hearing losses, but which cannot be heard by persons without such losses. Similarly, a person with normal hearing may be able to detect the difference between a plurality of bursts one of which is slighly longer (or shorter) in duration than the others, whereas a person with a hearing loss or who otherwise has a hearing problem, may not be able to detect such a difference. Finally, a person with normal hearing may be able to detect the difference between a plurality of tones one of which has a frequency which slightly higher or lower that the others, whereas a person with a hearing loss or who otherwise has a hearing problem, may not be able to detect such a difference.

DETAILED DESCRIPTION OF THE INVENTION

Figure 1:
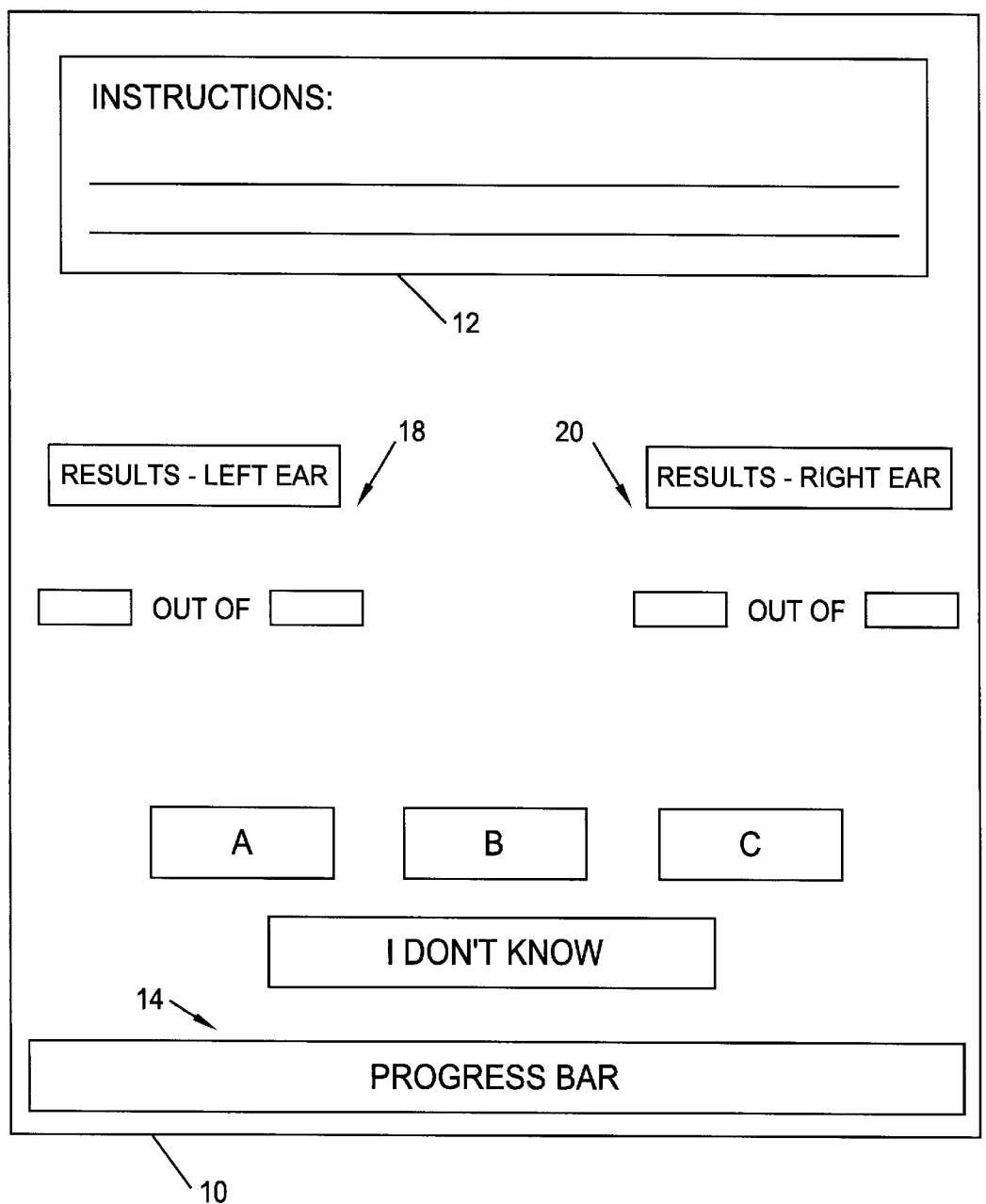
FIG. 1 is a diagram of the overall screen seen by a testee in accordance with the present invention.
Figure 2:
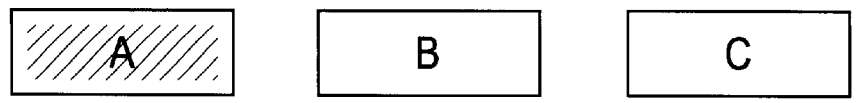
FIGS. 2 through 5 are a series of displays showing the visual highlighting which corresponds to various audio outputs of the testing of the present invention.
Figure 2:
Figure 3:
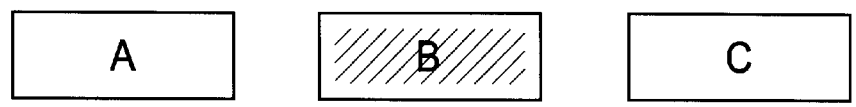
Figure 3:
Figure 4:
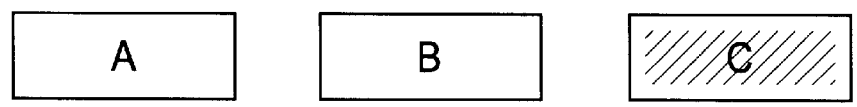
Figure 4:
Figure 5:
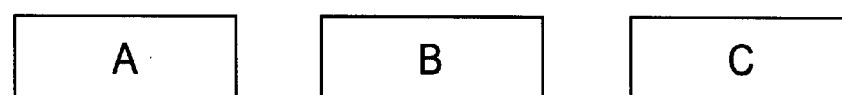
Figure 5:

FIG. 1 shows the overall screen which is produced on the testee's computer screen 10. An instruction box 12 contains a brief explanation of the procedures to be followed in a particular test. For example, in a preliminary test, the testee is instructed to use a mouse to click on a letter, A, B or C, if he or she comfortably hears a noise burst when one of those letters is highlighted, or to click the "I DON'T KNOW" box if either no sound is heard, or if the sound is not loud enough to be considered comfortable. A series of tests at varying levels of intensity are presented to the testee until the testee has consistently identified the correct letter, and assuming that the testee has followed the directions to choose a sound which is comfortable, the system identifies a base sound intensity based on the testee's correct answers. It should be noted that there are other ways of determining what intensity level is comfortable for the testee. For example, the testee could simply be presented with test sounds of varying decibel levels and choose one which the testee finds comfortable. The intensity or decibel level of any test will vary greatly depending upon the quality of the headphones used (or the level of background noise if no headphones are used), the quality of the computer system used by the testee, and perhaps the quality of the connection to the internet to which the testee has access.

While there are a number of ways in which the testee can set the sound output of the system to a comfortable intensity level for purposes of proceeding with substantive differential testing in accordance with the present invention, for some consumers (perhaps the very young or very old) the test pattern whereby the testee is instructed to select one of a plurality of areas which is highlighted in a coordinated way with the presentation of a sound having a comfortable level is a useful to familiarize the testee with the idea of coordinated highlighting and sound presentation used subsequently in substantive testing. Testing for a comfortable base intensity level on each ear of a user may, if a different level is arrived at for each ear, indicate that further testing should be done. Testing preferably proceeds in a sequence whereby substantive testing follows immediately after establishing a comfort level for that ear, so that one ear is tested completely before moving on to the other ear. However, an alternative whereby comfort levels for both ears are established before substantive differentiation testing proceeds.

It may be important, in order facilitate use of the system by younger or older users, to modify the screen by which the test sounds are presented to make the screen information more appealing or readable. For example, it may be helpful when using the system to test hearing of younger persons to include cartoon-like characters or bright colors to keep the child's attention focused on the screen. For older viewers, it may be helpful to make the print on the instructions large-type, and to make the areas where mouse-clicking is required larger than would be used with teens or middle-aged adults.

For any given test (preliminary or substantive), the progress bar 14 will show the testee by proportional shading how far along in the test the testee has progressed. Each test will include at least five parts during which the buttons A, B, C and "I DO NOT KNOW" will be sequentially highlighted, as shown in FIGS. 2 through 5.

When the preliminary testing is completed and a comfortable base intensity has been determined by the system or set by the testee, a different set of instructions will be displayed in the instruction box 12. The second set of instructions corresponds to the substative testing in which the testee is tested for his or her ability to differentiate between similar, but slightly different bursts or tones.

Figure 6:
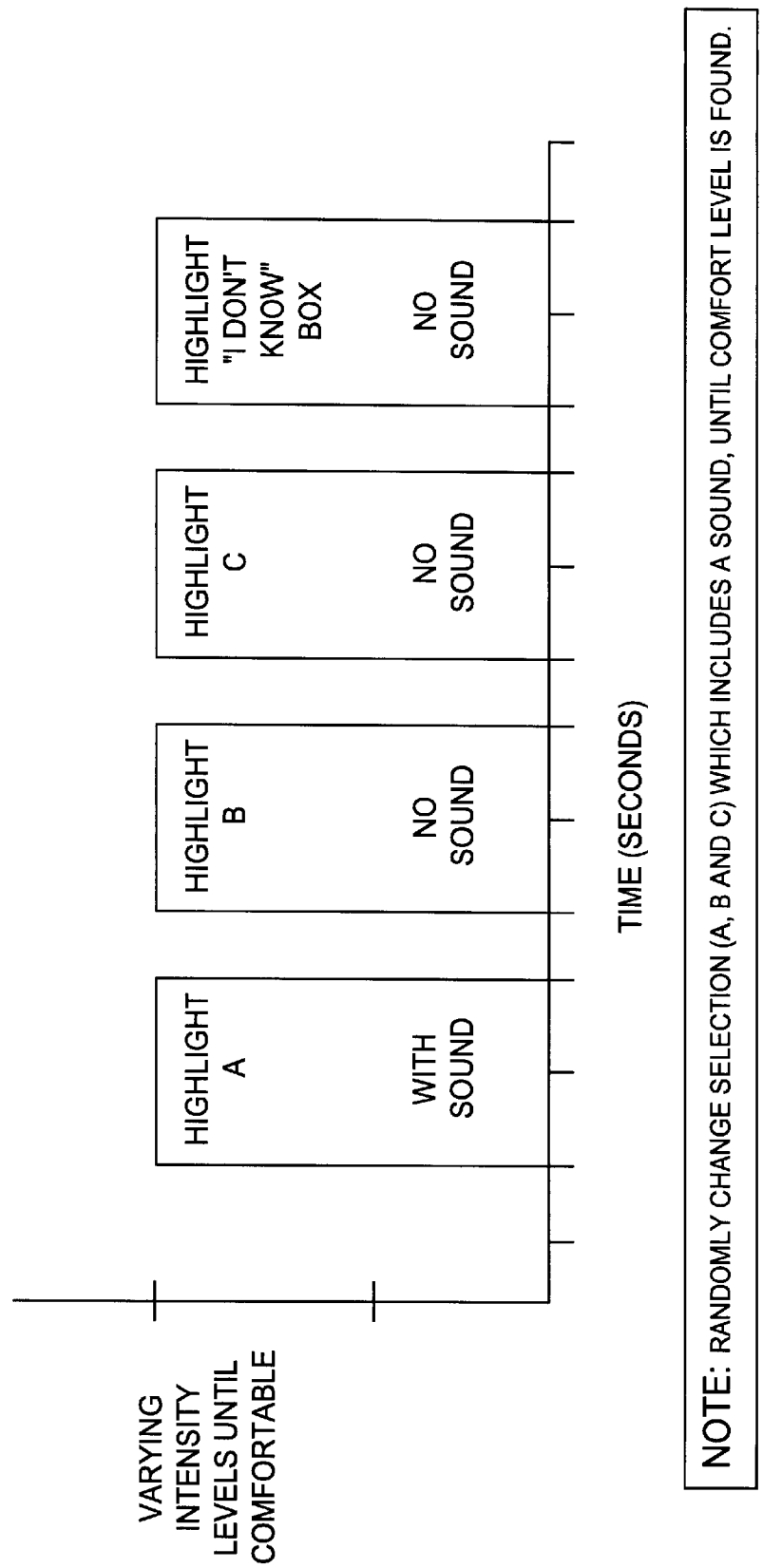
FIG. 6 is a graph showing a preliminary test as part of the present invention.

The substantive screening test presents to the testee a plurality, e.g., three consecutive noise bursts at the base intensity, one octave wide, at a particular frequency, e.g., 2 kHz, each having a duration of two seconds. The three consecutive bursts are syncronized with the visual highlighting of a letter which corresponds to the burst. As shown in FIG. 6, to test for the ability of the testee to distinguish between small differences in intensity levels, one of the three consecutive bursts includes a short miniburst of increased intensity. The minibust may be at an intensity of 1 db, 2 dB or 5 dB above the base intensity. The duration of the miniburst is 200 msec, but could be longer or shorter, depending on the degree to which the testee's sensitivity to differing sounds is to be tested. The individual being screened is asked to identify which of the three consecutive bursts contained the miniburst.

One preferred form of stimuli is a burst of sound, although with frequency as the differentiating factor, a precise tone may be preferred. A burst for purposes of the present invention is a mixed frequency stimulus which is centered about a base frequency, for example, 2 kHz, and may contain sounds above and below the base frequency, i.e., within 1-octave of the base frequency. In the examples shown in Figures, the bursts last about two seconds, but the duration may be varied. The sounds should, however, be similar in all respects except for the controlled variable, such as the insertion of a defined miniburst of increased intensity.

The test uses the three forced choice method discussed above. Three visual signals are presented on the computer monitor 10. Each signal is highlighted to coincide with the delivery of the bursts in sequence. Only one of the signals contains a miniburst. The testee indicates which signal houses the burst by clicking on the appropriate signal button, i.e., A, B, C or "Don't Know". The level of the burst is increased when an incorrect response is made and decreased when a correct response is made. The results are recorded when the same response is made four times. The result is defined as the average of the last two presentations. The test level obtained during this phase is used in the final testing session as a 19 dB below the start level.

The testing is dependent on the level of background noise and the type of headphones used. Circumaural headphones are recommended. With the development of techonology, insert earphones used in fixed and mobile internet sets/phone sets will be used. The use of loudspeakers precludes the testing of each ear separately and increases the influence of background noise. Testing in a noisy environment is not recommended. The testing is preferably conducted in a quiet environment, with no background noise e.g., radio, TV, traffic, printer etc.

FIG. 6 shows graphically the events that are included within one sub-part of a preliminary test. If the testee clicks the letter "A", he or she is credited with a correct answer. The sequence will be repeated at a given intensity level, but with a random association of the sound and one of the letters A, B or C. If the testee answers correctly four out of five times at one level of intensity, the base intensity for a subsequent screening test for that testee will be established at that intensity, since the testee has demonstrated an ability to comfortable hear the presentation of a stimulus.

Figure 7:
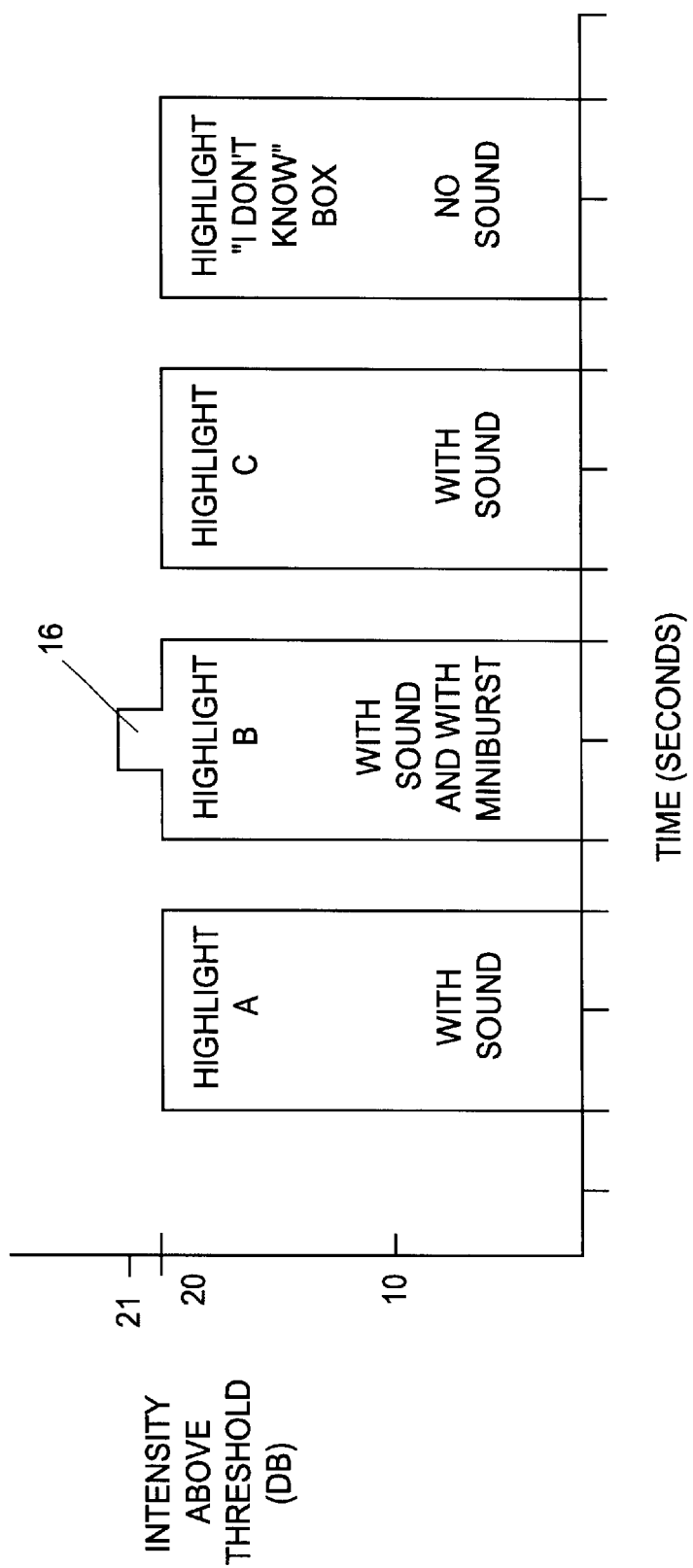
FIG. 7 is a graph showing a substantive screening test in accordance with the present invention in which a portion of the intensity of one of a plurality of bursts is different from the others.

FIG. 7 shows schematically a typical subpart of a screening test. In the example shown in FIG. 7, only the second of three consecutive bursts contains a miniburst. The miniburst is shorter in duration than the miniburst, and is 1 db higher in intensity than the burst during which it occurs. As an alternative, instead of a slight increase in the intensity, the second burst could include a miniburst in the form of a short duration decrease of 1 db within one of the burst choices presented to the testee. When presented with the series of bursts shown in FIG. 7, a click by the testee on the letter "B" will result in the testee being given credit for a correct answer. In FIG. 7, the burst which coincides with the highlighting of the letter B includes a miniburst 16 in which the intensity of the burst is momentarily elevated by a 1 db increment for a period of 200 milliseconds. No such miniburst is included within the other two bursts, however. The testing is repeated with the miniburst being included within one of the three bursts, A, B or C, randomly selected. The testee's ability to detect the presence of the miniburst is noted by a score in the boxes below the result indicators 18 and 20 (see FIG. 1). In this case, because small increases in intensity are detectible by persons suffering from sensorineural hearing losses, ability to which burst has the period of slight increase or decrease included within the burst is an indication that the testee has sensorineural hearing losses.

Figure 8:
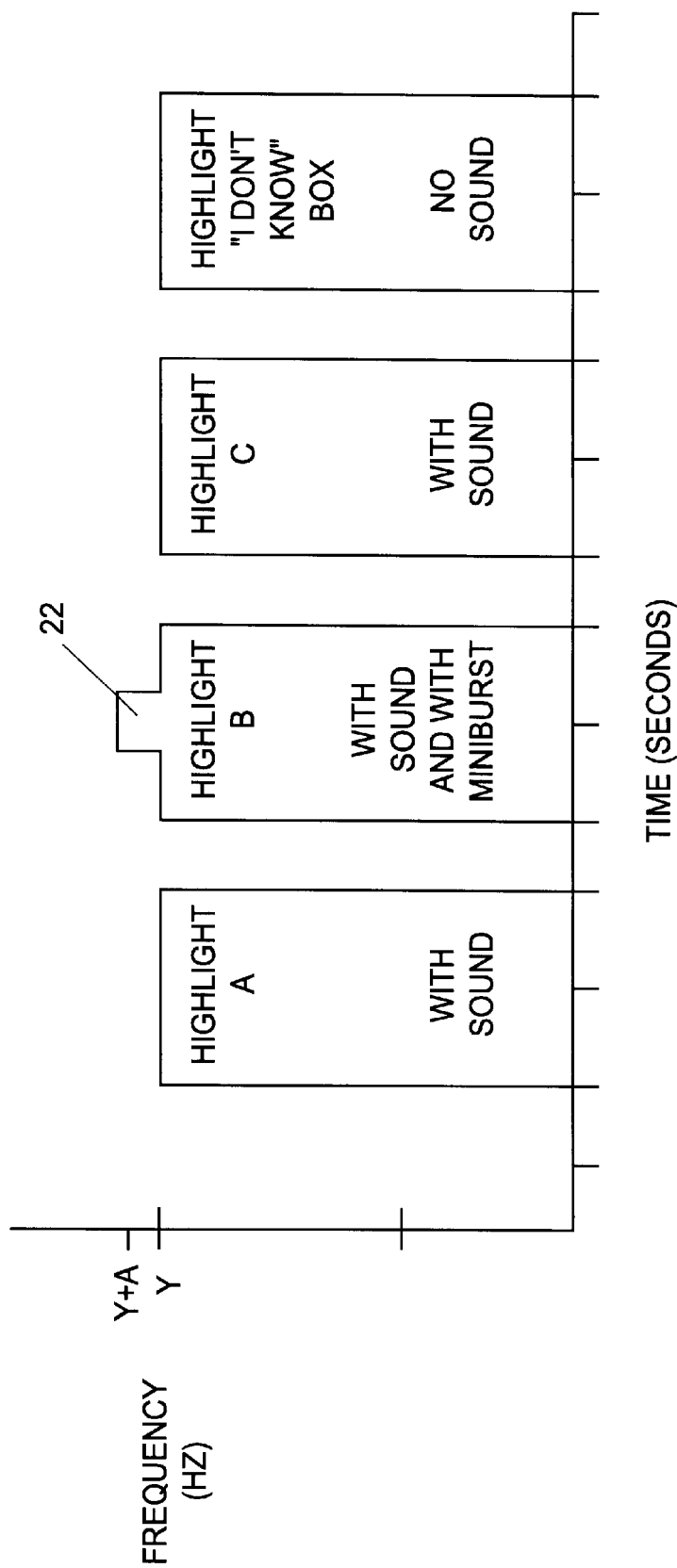
FIG. 8 is a graph showing a substantive screening test in accordance with the present invention in which a portion of the frequency of one of plurality of tones is higher than the others.

FIG. 8 shows another test which can be used to detect whether a testee can distiguish between different sounds. In the test depicted in FIG. 8 a testee is presented with three similar tones, one of which has a short duration deviation 22 of increased frequency stimulus as compared to the rest of the tone in which the deviation 22 is embedded, and as compared to the other tones not having any deviation. As with earlier described tests, the deviation 22 could be a short duration lowering of the frequency, as opposed to an increase. In this instance, the level of increase or decrease, the quantity "A" along the vertical axis in FIG. 8, is selected to be an amount of increase in frequency which should be detected by persons with normal hearing, so that failure to identify the burst or tone in which the increase or decrease is embedded may be used to identify a possible hearing problem which the testee may have.

Figure 9:
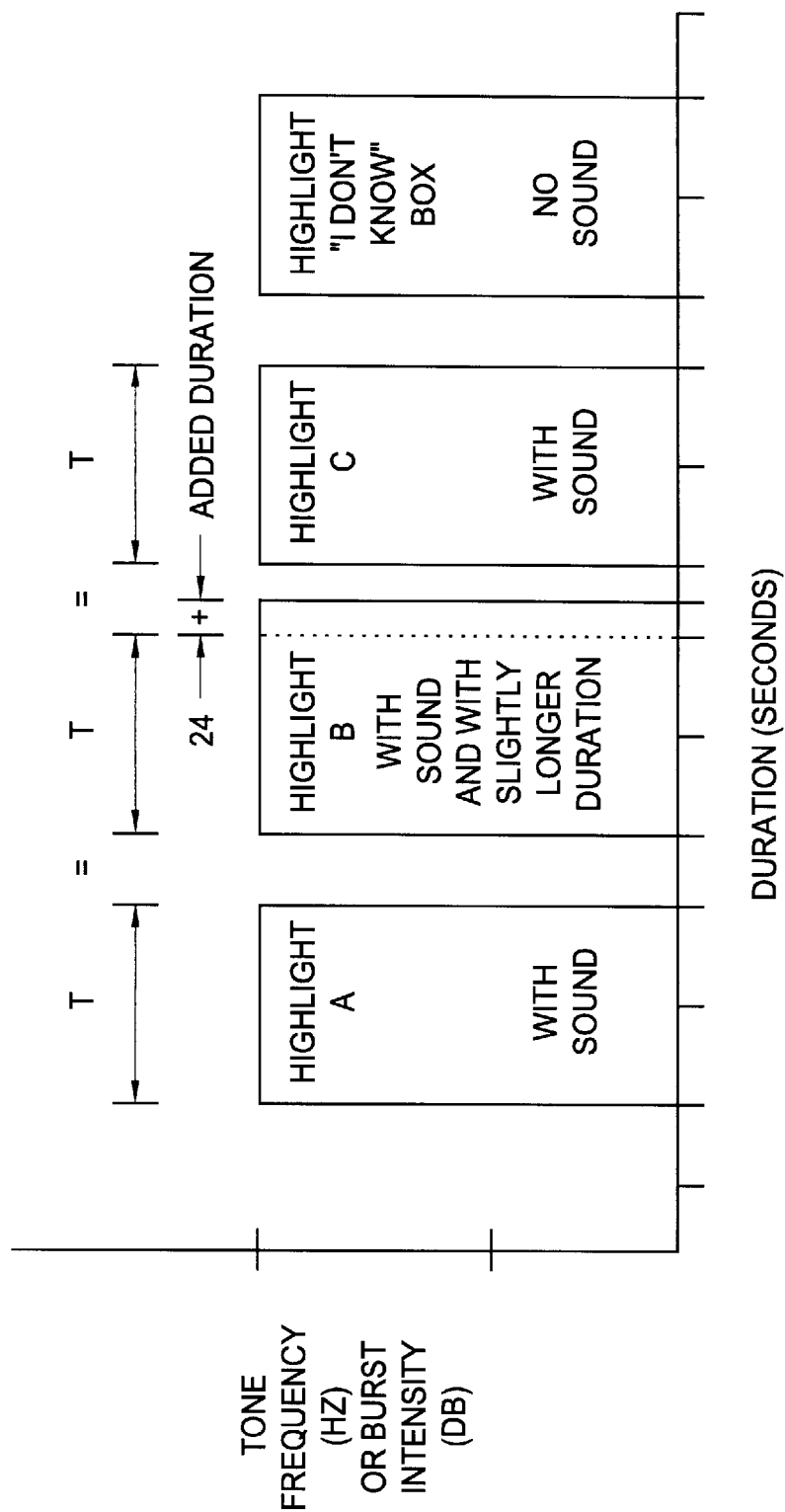
FIG. 9 is a graph showing a substantive screening test in accordance with the present invention in which the duration of one burst is longer than the others.

FIG. 9 shows yet another kind of test which may be performed as part of the present invention. The test of FIG. 9, like the earlier descibed tests, can be performed without the need to precisely calibrate the sound output equipment at the testee's site, because the sounds presented to the testee are again presented well above the threshhold of the testee. Thus, this test, like the earlier descibed tests of FIGS. 7 and 8, is suitable for internet applications. As can be seen in FIG. 9, one of a plurality of similar bursts or tones A, B or C (in this case B) is slightly longer in duration that the others presented to the the testee. The testee is asked to identify the sound which is different from the others in the plurality presented. The length of the addional duration will be set such that persons with normal hearing ability will be able to recognize and identify that tone or burst as being different, i.e. longer in duration, that the other tones or bursts presented in a given series. The vertical axis indicates that the test of FIG. 9 may be presented with tones at constant (or perhaps varying—not shown) frequency, or with bursts at constant (or varying—not shown) intensity. The important variable in the test of FIG. 9 is that of duration; in the example shown the duraiton of selections A and C are equal in time (T), and the second selection, B, has a duration of T+, where the added duration (+) is selected to allow persons of normal hearing to identify B as different from A and C in that it contains a deviation 24 in the form of a slightly longer duration. The difference could, however, be that selection B is shorter, instead of longer, in duration.

The testing in accordance with the present invention, such as is shown in FIGS. 7, 8 and 9, is preferably done on each ear of the testee independently, one ear at a time, with a base intensity level being established for each ear. As was discussed earlier in connection with the identificaion of a different comfort level for each ear, if testing of a testee in any test results in widely different results from one ear to the next, this may be noted as indicating a hearing problem which the testee may want to have further investigated.

The screeing test of the present invention includes a preliminary test and a second substantive test. In each case, a multiple or forced choice technique is used. To help assure statistical accuracy in each case, i.e., in the preliminary and substantive testing, the testee must score at an eighty percent level in order to pass the test. In the example shown in FIG. 1, the method of response is a forced choice method, three selections and a "Do Not Know" answer (a total of four choices). The method compensates for a chance score by using 80 percent (e.g., four out of five correct answers) as the performance criteria.

The present invention is particularly well-suited for use as part of a hearing health (or general heath) an interactive website operated by a server with one or more programs having instructions in accordance with the present invention. Typically, the program of the present invention will be accessed via internet. However, the testing program arranged and presented in accordance the present invention may be circulated in other ways. For example, rather than having having to gain access to the internet, the interactive progam of sound presentation and selection by the testee, could be stored on a floppy disk and could be used with any computer having a sound card. Computers such as laptops are often equipped with sound cards and earphone jacks. Such a computer with software embodying the present invention could be taken to remote locations. At such locations, using only battery power, a laptop with a program containing instructions in accordance with the present invention could be used to conduct testing and could be used to perform hearing screening tests in places where hearing clinics with more sophisitcated hearing test equipment are hudreds of miles away. In this way, screening tests and indentification of hearing problems may be performed for patients who would otherwise be unable to receive such services.

While the invention has been disclosed by reference to a particular set of examples, it will be clear to those skilled in the art of audiological testing and network communications that a number of variations, modifications and improvements may be made to the disclosed examples without departing from the spirit and scope of the present invention. All such variations, modifications and improvements are intended to be included within the scope of the claims set forth below.

What is claimed is:

1. A system for providing remote screening for patients concerned about potential hearing loss comprising a test program usable on a network said program including a first test in which a base intensity is established for a testee, said first test including a series of subparts in which one audible output signal is simultaneously presented with one of a plurality of highlighted visual output signals, said program selecting a base intensity level on the basis of accurate selection by said testee of which said plurality of visual output signals has associated therewith an audio output signal, said program including a second test in which a series of visual output signals and corresponding simultaneous audio output signals are presented to said testee at the base intensity determined by said first test, the audio output of one of said corresponding and simultaneous audio output signals containing a sound similar to but different from other sounds in said series, said program keeping score of the ability of said testee to accurately select which of said corresponding and simultaneous audio output signals differs from other sounds in said series.

2. A system in accordance with claim 1 wherein at least a portion said sound which is similar to but different from other sounds in said series is different in its intensity from said other sounds.

3. A system in accordance with claim 1 wherein at least a portion said sound which is similar to but different from other sounds in said series is different in its frequency from said other sounds.

4. A system in accordance with claim 1 wherein at least a portion said sound which is similar to but different from other sounds in said series is different in its duration from said other sounds.

5. A system in accordance with claim 1 wherein at least a portion said sound which is similar to but different from other sounds in said series is greater in intensity than said other sounds.

6. A system in accordance with claim 1 wherein at least a portion said sound which is similar to but different from other sounds in said series is greater in frequency than said other sounds.

7. A system in accordance with claim 1 wherein at least a portion said sound which is similar to but different from other sounds in said series is greater in duration than said other sounds.

8. A system in accordance with claim 1 wherein:
said system includes a display of said score,
said system being capable of printing, storing and or forwarding said score by e:mail.

9. A system in accordance with claim 1 wherein:
said program performs a first test on a first ear of a testee, followed by a second test on said first ear of said testee, and said program subsequently performs the first test on a second ear of said testee followed by the second test on the second ear of said testee.

10. A system in accordance with claim 1 wherein said one of said corresponding and simultaneous audio output signals containing a sound similar to but different from other sounds in said series is able to be detected substantially only by persons with a hearing problem.

11. A system in accordance with claim 1 wherein said one of said corresponding and simultaneous audio output signals containing a sound similar to but different from other sounds in said series is able to be detected substantially only by persons without a hearing problem.

12. A computer-usable medium containing a program for conducting screening tests for hearing ability, said program comprising:
instructions for initiating a screening test in which a plurality of sounds are presented to a testee,
instructions for generating a first output to a testee including a description of a first set of steps to be taken by said testee for the purpose of establishing a comfortable and readily audible intensity level of stimuli received by said testee,
instructions for presenting a first series of synchronous visual and audible outputs to said testee, said audible outputs including sounds at varying levels of intensity, instructions for receiving first inputs from said testee in response to said first series of outputs and for determining a comfortable test intensity level for said testee, instructions for generating a second output to a testee including a description of a second set of steps to be taken by said testee for the purpose of establishing whether said testee is able to identify which one of plurality of similar audible stimuli received by said testee is different from others in said plurality, instructions for presenting a second series of synchronous visual and audible outputs to said testee at an intensity level based upon said first inputs, said second series of synchronous visual and audible outputs including a plurality of similar sounds are presented to a testee with one of said plurality of similar sounds containing at least a portion of modified sound with respect to other sounds in said plurality, instructions for receiving second input from said testee in response to said second series of synchronous visual and audible outputs and for determining an ability of said testee to identify said modified sound, instructions for making a record of said second inputs and keeping track of when said testee is able or not able to correctly identify said slightly modified sound.

13. A computer-usable medium in accordance with claim 12 in which said program includes a series of pluralities of sounds, each plurality having one modified sound which differs from other sounds in said plurality, said modified sound being different in that at least a portion of said modified sound is different in intensity from other sounds in said plurality.

14. A computer-usable medium in accordance with claim 12 in which said program includes a series of pluralities of sounds, each plurality having one modified sound which differs from other sounds in said plurality, said modified sound being different in that at least a portion of said modified sound is different in frequency from other sounds in said plurality.

15. A computer-usable medium in accordance with claim 12 in which said program includes a series of pluralities of sounds, each plurality having one modified sound which differs from other sounds in said plurality, said modified sound being different in that at least a portion of said modified sound is different in duration from other sounds in said plurality.

16. A computer-usable medium in accordance with claim 12 in which said program includes a series of pluralities of sounds, each plurality having one modified sound which differs from other sounds in said plurality, said modified sound being different in that at least a portion of said modified sound is greater in intensity than other sounds in said plurality.

17. A computer-usable medium in accordance with claim 12 in which said program includes a series of pluralities of sounds, each plurality having one modified sound which differs from other sounds in said plurality, said modified sound being different in that at least a portion of said modified sound is greater in frequency than other sounds in said plurality.

18. A computer-usable medium in accordance with claim 12 in which said program includes a series of pluralities of sounds, each plurality having one modified sound which differs from other sounds in said plurality, said modified sound being different in that at least a portion of said modified sound is greater in duration than other sounds in said plurality.

19. A system in accordance with claim 1 where in the network is the Internet.

* * * * *